United States Patent [19]

Lee

[11] Patent Number: 5,089,266
[45] Date of Patent: Feb. 18, 1992

[54] NON-TOXIC INSECTICIDE COMPOSITION AND METHOD FOR KILLING SPECIFIC INSECTS

[76] Inventor: Merlin Lee, 4607 S. Bradley Rd., Orcutt, Calif. 93455

[21] Appl. No.: 419,455

[22] Filed: Oct. 10, 1989

[51] Int. Cl.$^5$ ............................................. A01N 25/04
[52] U.S. Cl. .................................. 424/407; 424/405; 106/170; 106/197.2; 514/57; 514/781; 47/58; 47/DIG. 11
[58] Field of Search .................. 424/405, 407; 514/57, 514/781; 47/58, DIG. 11; 106/170, 197.2

[56] References Cited

U.S. PATENT DOCUMENTS

| | | | |
|---|---|---|---|
| 4,652,574 | 3/1987 | Kato et al. | 514/347 |
| 4,755,397 | 7/1988 | Eden et al. | 71/64.11 |
| 4,762,718 | 8/1988 | Marks | 424/407 |
| 4,804,683 | 2/1989 | Steltenkamp | 514/613 |
| 4,812,445 | 3/1989 | Eden et al. | 514/60 |
| 4,820,698 | 4/1989 | Degenhardt et al. | 514/102 |
| 4,948,798 | 8/1990 | Gsell | 514/341 |
| 4,954,316 | 9/1990 | Globus | 424/405 |
| 4,973,589 | 11/1990 | Barnett et al. | 514/245 |
| 4,983,392 | 1/1991 | Robinson | 514/177 |
| 4,985,063 | 1/1991 | Fischer et al. | 514/256 |

*Primary Examiner*—Ronald W. Griffin
*Attorney, Agent, or Firm*—Allegretti & Witcoff, Ltd.

[57] ABSTRACT

Non-toxic insecticide composition for killing aphids, leafhoppers and spider mites comprising an aqueous solution of sodium carboxymethylcellulose having a preferred viscosity of 100 to 500 centistokes. The solution is used to entrap the insects or the spiracles of the tracheal system.

11 Claims, No Drawings

NON-TOXIC INSECTICIDE COMPOSITION AND METHOD FOR KILLING SPECIFIC INSECTS

BACKGROUND OF THE INVENTION

This invention relates to a non-toxic insecticide composition which is useful in killing aphids, leafhoppers and spider mites. These insects belong to a large order (homoptera) of insects having sucking mouth parts. These insects have plagued farmers for many years. Aphids, sometimes called plant lice, reproduce in enormous quantities in a short period of time and destroy many crops. They cause curling or wilting of cultivated plants by sucking sap from the stems or leaves. Aphids also destroy crops by carrying viruses such as lettuce mosaic virus, especially harmful to this crop in the Salinas Valley of California. Aphids are also notoriously effective vectors for zucchini yellow mosaic virus which can produce a total crop failure. There are many species of aphids, each of which is identified colloquially by their host plant. For example, apple aphid, cotton aphid, rose aphid, etc. Most aphids go through winter on their specific plants in the egg stage.

Leafhoppers feed on leaves and are also vectors of organisms that cause plant diseases. These insects suck the sap from the leaves and reduce or destroy the chlorophyll whereupon the leaves turn yellow or brown.

Spider mites exist in various species which do serious damage to orchard trees, field crops and greenhouse plants. Eggs laid on the plants hatch in four or five days and the mites mature to adult in about three weeks.

All of the foregoing insects are born or hatched on the plants and the insecticide, therefor, must be applied to the plants which are infested with the insects.

Government regulations set limits on the amounts of chemical insecticide residues left on fruits and vegetables to insure that they are well below danger levels. According to the Environmental Protection Agency, use of pesticides, fungicides, herbicides, insecticides and plant growth regulators have more than doubled during the period 1969–1989 to about 820 million pounds annually. This invention relates to non-toxic insecticides which provide a solution to the problems associated with toxic agricultural insecticides.

THE PRIOR ART

Toxic insecticides now being used to control insects operate by attacking the central nervous system and kill by paralysis or they attack the metabolic cycle of the insect and disrupt the process causing death. Unfortunately, all animals have central nervous systems and utilize the same metabolic cycle, hence what kills the insect can also kill other animals that contact the insecticide. These chemicals put at risk persons who apply them in the fields. Their use increases liability insurance rates for farmers. Toxic chemical insecticides kill beneficial insects as well as those which are crop destructive. Commercial pesticides have been developed to maximize the exposure to the target pest and minimize the exposure to other animals, but the results have been disappointing.

Toxic chemical compounds may be initially effective, but over time, the insects develop an immunity which means that the active chemical in the insecticide composition must be used in larger and larger quantities or that new compositions must be developed. There are literally hundreds of organic compounds available which are used to kill insects. These include organic derivatives of phosphorous, of carbamic acid, of nitrophenols and other miscellaneous compounds. These compounds are mixed with anti-caking agents, corn starch, wetting agents, diluents and other ingredients to facilitate their preparation and use in application to the crops by farmers. U.S. Pat. No. 4,307,115 is a typical insecticide containing 90–94% methomyl as the active ingredient in admixture with measured quantities of silicas, corn starch, clays, and surfactants totaling the balance of 10–6% by weight. In Example 2 of this patent, the composition contains 0.1% methyl cellulose. These compositions are water dispersible and are applied to crops as aqueous dispersions. The minor additives in these compositions are added merely for the purpose of facilitating mixing the active ingredient with water. These additives are not effective, in the insecticide compositions disclosed, for killing insects. Killing occurs only by contact with the active ingredient, methomyl.

Active substances are also used as dusts in solid carriers such as kaolin, chalk, limestone, sodium and potassium alumina silicates, corn meals, sawdust, cellulose powder, activated charcoal and the like. The dust is scattered on plants infested with the harmful insects.

THE INVENTION

The object of the present invention is to provide a non-poisonous insecticide which is completely effective in killing insects, leaves no poison of any kind on the crops, is economical, easy to dissolve and to apply without special equipment. Furthermore, the insecticide is not phytotoxic or harmful to the environment. These objects are achieved by using a composition which kills the insects by physical rather than chemical means. The composition is sticky or tacky. It captures the insects and holds them, entrapped, until they die. Furthermore, the compositions are film forming and when sprayed on the insects, the film deposited blocks the spiracles of the tracheal system of the insect and kills by asphyxiation. Aphids cling lightly to the infected plant and some are blown off by the spray. But the adhesive film with which they are coated cuts off the supply of oxygen normally taken in through the tracheal system. The films of the invention are not only non-toxic, but are also biodegradable.

The compositions of the invention consist of a tacky film-forming solution of sodium carboxymethyl cellulose which can be sprayed on the plants using conventional agricultural spraying equipment. The solution is sprayed in small droplets, having a particle size of 50–400 microns, which deposit on the leaves of the plant and form a film which entraps the insects and covers their eggs. Since the sodium carboxymethyl cellulose is soluble in cold water, farmers can prepare the solutions on the farm in 50 or 100 gallon tank without the expense and trouble of heating the water. The water preferably contains a surfactant to reduce the surface tension and facilitate wetting of the insects and the leaves of the plant. The sodium carboxymethyl cellulose is added as a powder and dissolves readily with agitation. The viscosity of the polymer solution ranges between about 10 and about 3000 centistokes (cSt), preferably 100 and 500 cSt. Below 10 cSt the droplets do not adhere to the insects and the plants, but run off. No film is formed over the insects. Above about 3000 cSt the surface tension is so great that the film formed is discontinuous so many of the insects do not become immersed in the film. Consequently, the viscosity of the solution is important in preparing the solutions of the invention.

Sodium carboxymethyl cellulose (CMC) is an anionic cellulose ether available in powder or granule form having a particle size of 50 to 200 microns. CMC is available commercially in a DS range of 0.38 to 1.4, DS being the degree of substitution of —CH$_2$COONa groups on the —OH groups of the beta-anhydrogluscose rings comprising the cellulose ether polymer. There are three hydroxyl groups on each ring so the maximum value of DS is three. As the DS of the CMC increases, the viscosity of solutions prepared from the CMC increases. CMC powders are produced commercially in various viscosities. The viscosity is expressed as the intrinsic viscosity of a 2% solution measured at room temperature. The commercial CMC polymers used to illustrate this invention are designated by their viscosity ranges, e.g. 10–20, 400–800, and 3000–6000 centipoises. Mixtures of CMC having different intrinsic viscosities can be used for purposes of the invention so long as the resulting solution has a viscosity within the specified range. As indicated, this range is between 10 and 3000 cSt, kinetic viscosity. (1 centipoise equals 1 cSt times the density of the liquid.)

CMC is available commercially and is produced by a number of different manufacturers. Commercial products used in connection with this invention have been obtained from Sigma Chemical Co. in St. Louis as product # C8758 (low viscosity CMC, 10–20 centipoises) and product # C4888 (medium viscosity CMC, 4–800 centipoises). The higher viscosity CMC (3000–6000 centipoises) can be obtained from Aldrich Chemical Co., Milwaukee, Wis. under the product # 32000306-3). CMC is recognized by government regulations as safe for use in foods (21 CFR 182.1745).

To be effective in killing the insects, the solution must produce a tacky film which can be sprayed through the nozzle of conventional agricultural spray equipment. As the viscosity of the solution approaches the 3000 kinetic viscosity range, the spraying pressure must be increased in order to produce droplets of the desired size. Agricultural spraying tanks are equipped with hollow conical nozzles and are operated in accordance with the invention using pressures between about 100 psi and 600 psi. The droplet size will range from 50 microns to 400 microns depending upon the solid content and the viscosity of the solution being sprayed.

To improve the wetting of the insects and the leaves of the plants, a surface active agent should be added to the water. The water, in which all solutions of the invention are prepared, contains about 0–1% of a surfactant wetting agent, e.g. alkyl/aryl polyether alcohols, polyethylene oxide esters (or ethers) of fatty acids, alkyl/aryl sulfonates, alkyl sulfates and the like. These surface active agents are well known in the art for use in preparing dispersions of insecticides. In the solutions of the invention, the surfactants assist in causing the solution droplets to spread out on waxy leaves and penetrate the waxy protective coating on the insects and their eggs.

The films of the invention are hygroscopic and pick up moisture from the air. In some instances, it is desirable to maintain the film in a wet and tacky condition for up to 24 hours to trap insects that were not on the plant at the time of spraying. This is done by adding a non-toxic salt such as lithium chloride, lithium acetate or potassium acetate in the amount of 0–1.5% by weight.

SPECIFIC EXAMPLES

EXAMPLE 1

A solution was prepared by dissolving 5 grams of low density CMC (10–20 centipoises) and 5 grams of medium viscosity CMC (400–800 centipoises) in 480 grams of water. The water contained 0.8% of surfactant (Amway APSA-80). The solution was mixed with an agitator to produce a kinetic viscosity of 136.4 cSt. The solution was put into a conventional agricultural sprayer and sprayed through a hollow cone spray nozzle at a pressure of 250 psi. The droplet size was 100–150 microns.

The solution was sprayed on thistles having myriad aphids on the stems and leaves. The solution was deposited on the stems and leaves of the thistle. Immediately after spraying, sections of the stems with leaves attached were removed and viewed through a dissecting microscope. 95% of the aphids on the plant had died with no sign of any struggle. It appears that they were asphyxiated by reason of the sticky film covering or clogging their spiracles. The other 5% struggled and lost extremities ending up in grotesque positions in death. The examination as confirmed by photographs taken before and after spraying which photographs showed clearly at 30 times actual size the conditions of the insects at both stages. Since aphids perch very lightly on a plant, they have limited ability to cling. Therefore, the force of the spray knocked about one third of the aphids off the plant. To determine the condition of these aphids a white backdrop was placed behind the plant on which the removed aphids were deposited. Inspection of these insects indicated that they, too, had died by reason of asphyxiation.

EXAMPLE 2

A solution was prepared by dissolving with agitation 5 grams of high viscosity CMC (3000–6000 centipoises) and 5 grams of lithium chloride in 480 grams of water containing a surfactant as in Example 1. This solution had a kinetic viscosity of 3038 cSt. The lithium chloride serves to keep the solution "wet" for a longer period of time by slowing the rate of evaporation. The presence of lithium chloride reduces the viscosity dramatically and for this reason the higher viscosity starting material was used. The solution was put into a conventional agricultural sprayer and sprayed through a hollow cone nozzle. The spraying pressure was 600 psi and the droplet size was 300–400 microns.

The solution was sprayed on bush beans infected with potato leafhoppers (empoascafabae). Examination of the plant under magnification after about four hours indicated that all of the leafhoppers had been killed.

Leafhoppers are disturbed by personnel and equipment. By extending the period during which the film remains "wet" and tacky, the leafhoppers which left the plant are trapped when they return.

EXAMPLE 3

A solution was prepared by dissolving 10 grams of low viscosity CMC (10–20 centipoises) in 480 grams of water containing a surfactant as in Example 1. The solution had a kinetic viscosity of 10.19 cSt. The solution was sprayed from a conventional sprayer as in Example 1 using a pressure of 100 psi. The droplet size was between 50 and 100 microns.

This solution was sprayed on rose bushes infested with spider mites (prostigmata). Examination under magnification two hours after spraying indicated that all spider mites on the plant had been killed.

From the foregoing, it is apparent that this invention provides a non-toxic biodegradable effective insecticide which does not damage the most delicate plants or their leaves. It is inexpensive and kills insects by physical rather than chemical means. It was highly unexpected that this edible material would kill insects by physical means.

What is claimed is:

1. A non-toxic insecticide composition for killing aphids, leafhoppers and spider mites comprising an aqueous solution of sodium carboxymethyl cellulose having a kinetic viscosity of about 10 to about 3000 centistokes and which produces a tacky hygroscopic film.

2. The composition of claim 1 having a viscosity of between 100 and 500 centistokes.

3. The composition of claim 1 in which said sodium carboxymethyl cellulose has a degree of substitution equal to a value between 0.65 and 0.85.

4. The composition of claim 1 in which said sodium carboxymethyl cellulose (CMC) from which said solution is prepared consists essentially of a mixture of low intrinsic viscosity CMC (10-20 centipoises) and medium intrinsic viscosity CMC (400-800 centipoises).

5. The composition of claim 1 in which said solution is prepared by dissolving in water about 1% of sodium carboxymethyl cellulose having an intrinsic viscosity of 3000-6000 centipoises and 0-1% of a surfactant, said percentages being by weight.

6. A method for killing aphids, leafhoppers and spider mites which comprises spraying the film forming solution of claim 1 on a plant carrying said insects to entrap said insects and to block the spiracles of the tracheal system.

7. The method of claim 6 in which said solution is sprayed in the form of droplets 50 to 100 microns in size.

8. Composition of claim 1 which contains 0-1% by weight of a surfactant.

9. A method killing aphids, leafhoppers and spider mites which comprises spraying an aqueous film-forming solution of sodium carboxymethyl cellulose containing 0-1% by weight of a surfactant and having a kinetic viscosity of 10-3000 centistokes on a plant carrying said insects to entrap said insects and to block the spiracles of the tracheal system.

10. The method of claim 9 in which said solution has a kinetic viscosity of about 135 centistokes and is sprayed in the form of droplets having a particle size of 100-150 microns.

11. The method of claim 9 in which said solution is prepared from sodium carboxymethyl cellulose having an intrinsic viscosity of 3000-6000 centipoises and includes 0-1.5% of a non-toxic salt to reduce the rate of evaporation of the solution.

* * * * *